United States Patent [19]
Attridge

[11] Patent Number: 5,166,515
[45] Date of Patent: Nov. 24, 1992

[54] METHOD OF OPTICAL ANALYSIS OF A FLUID INCLUDING AN OPTICAL WAVEGUIDE

[75] Inventor: John W. Attridge, Weybridge, United Kingdom

[73] Assignee: Applied Research Systems ARS Holding, N.V., Netherlands Antilles

[21] Appl. No.: 623,817

[22] PCT Filed: Jun. 21, 1990

[86] PCT No.: PCT/GB90/00953

§ 371 Date: Dec. 19, 1990

§ 102(e) Date: Dec. 19, 1990

[87] PCT Pub. No.: WO90/15985

PCT Pub. Date: Dec. 27, 1990

[30] Foreign Application Priority Data

Jun. 22, 1989 [GB] United Kingdom .................. 8914343
Apr. 11, 1990 [GB] United Kingdom .................. 9008261

[51] Int. Cl.⁵ .............................................. H01J 5/16
[52] U.S. Cl. ............................ 250/227.25; 250/458.1; 356/246

[58] Field of Search ............. 250/226, 227.11, 227.25, 250/227.31, 458.1; 356/244, 246

[56] References Cited

U.S. PATENT DOCUMENTS

| | | | |
|---|---|---|---|
| 4,668,636 | 5/1987 | Ringrose et al. | 356/246 |
| 4,810,658 | 3/1989 | Shanks et al. | 250/227.31 |
| 4,844,869 | 7/1989 | Glass | 356/246 |
| 4,880,752 | 11/1989 | Keck et al. | 250/458.1 |

Primary Examiner—David C. Nelms
Attorney, Agent, or Firm—Ostrolenk, Faber, Gerb & Soffen

[57] ABSTRACT

The invention relates to a method of optical analysis which can advantageously be used in conjunction with optical assay techniques, particularly those wherein evanescent signals are to be analysed. The method makes use of the properties of an optical structure (described herein) which allows easy angular discrimination of optical signals emerging from a test object. The invention also relates to apparatus for use in said methods.

18 Claims, 3 Drawing Sheets

METHOD OF OPTICAL ANALYSIS OF A FLUID INCLUDING AN OPTICAL WAVEGUIDE

This invention relates to methods of optical analysis of evanescent signals and to apparatus for use in such methods.

More particularly, the invention relates to methods of, and apparatus for, detecting evanescent signals produced during ligand/specific binding partner assay procedures, particularly immunoassays.

The prior art contains various disclosures of analytical devices for handling and metering small volumes of test samples, and for the use of such devices in methods of optical analysis.

For example, U.S. Pat. No. 3,939,350 describes optical measurement of fluorescent material bound to the surface of a solid transparent prism by a method involving single total internal reflection and interaction of the evanescent wave at the surface of the prism with the bound material.

EP-A-75353 makes reference to the exponentially decaying (evanescent) external radiation due to light which is propagated longitudinally in a fibre, and its interaction with coatings.

EP-A-170376 describes, inter alia, methods of optical analysis of fluorescence emerging from a waveguide which is part of a chemical test device, whilst EP-A-171148 describes in detail certain chemical test devices, namely fluorescence capillary fill devices, and methods for their manufacture.

As described in EP-A-171148, a fluorescence capillary fill device (hereinafter FCFD) typically consists of two pieces of transparent material, e.g. glass, separated by a narrow gap. One plate acts as an optical waveguide and carries an immobilized reagent appropriate to the test to be carried out in the device. For use in an immunoassay, the immobilized reagent may for example be an antibody to an antigen desired to be detected and one of the plates may carry a dissoluble reagent comprising antigen labelled with a fluorescent dye. When a sample is presented to one end of the FCFD it is drawn into the gap by capillary action and dissolves the reagent. In a competition assay, the fluorescently labelled antigen will compete with sample antigen for the limited number of antibody binding sites immobilized on the waveguide. Because the capillary gap is narrow (typically about 100 microns) the reaction will generally go to completion in a short time, possibly less than 5 minutes. In a sandwich assay, the waveguide will carry a specific binding partner for the ligand desired to be detected and one of the plates will carry a dissoluble reagent comprising a further specific binding partner labelled with a fluorescent dye. In a sandwich immunoassay for an antigen, a sample antigen will form a sandwich complex with a fluorescently labelled antibody and an antibody immobilized on the waveguide. Thus the amount of fluorescently labelled antibody which becomes indirectly bound to the waveguide by virtue of complex formation will be a function of the concentration of antigen in the sample.

The term "antigen" as used herein will be understood to include both antigenic species (for example, proteins, bacteria, bacterial fragments, cells, cell fragments and viruses) and haptens which may be rendered antigenic under suitable conditions.

When using an FCFD in an assay, evanescent wave coupling avoids the need for a separation or washing step. When the labelled reagent is optically excited by a light source of suitable wavelength, fluorescence emission occurs both from fluorophores in the liquid phase and from fluorophores bound, directly or indirectly, to the waveguide. The optical properties of the media involved are such that most of the fluorescence arising from surface-bound fluorophores emerges from the transverse edge of said waveguide at angles to the normal whose magnitude is less than the magnitude of a certain angle $\alpha$, whilst substantially all of the fluorescence arising from fluorophores in the liquid phase emerges from the edge of said waveguide at angles to the normal whose magnitude is greater than the magnitude of $\alpha$ ($\alpha$ being such that $-\frac{1}{2}\pi < \alpha < \frac{1}{2}\pi$). The value of $\alpha$ depends on the refractive indices of the liquid solution in the cavity and of the material of the waveguide and on the wavelengths of light involved, but is given approximately by $$\alpha \approx \arcsin(n_2^2 - n_1^2)^{\frac{1}{2}},$$

wherein $n_1$ represents the refractive index of the liquid phase and $n_2$ represents the refractive index of the solid waveguide. Thus, under ideal conditions, angular discrimination of fluorescence emerging from the edge of the waveguide would be sufficient to separate the different emission signals.

Although the discussion herein is conducted with reference to angles to the normal whose magnitude is compared to the magnitude of $\alpha$ as defined herein, it should be understood that these angles may deviate from said normal in either a positive or negative sense.

In practice, however, the sensitivity of assays employing simple angular discrimination of fluorescence emission is limited by a number of experimental factors including, inter alia: inefficient filtering out of the light of excitation wavelength and secondary fluorescence in all directions from the optical filter (typically of colloidal glass); and aberration of the lenses used to focus the fluorescence emission onto the detectors.

Surprisingly, we have now found that assay techniques such as those described above can be implemented without the need for excessive filtering or costly and complex systems of lenses, by using instead an additional optical structure placed close to the edge of said waveguide to provide efficient angular discrimination of fluorescence emission, or by analogy phosphorescence or luminescence emission Thus, according to one aspect of the invention we provide a method of optical analysis of a test sample having fluorescent, phosphorescent or luminescent properties, which sample is partly in a liquid phase and partly bound, directly or indirectly, to an adjacent solid surface, comprising the steps of
(i) providing as said solid surface a surface of a transparent (at least at the wavelengths of radiation involved in the analysis) solid optical waveguide;
(ii) measuring light from the sample material bound to said solid surface which has propagated through said waveguide and emerged therefrom at an angle deviating from the optical axis of said waveguide by an angle having a magnitude less than the magnitude of $\alpha$ where $$\alpha \approx \arcsin(n_2^2 - n_1^2)^{\frac{1}{2}},$$

wherein $n_2$ is the refractive index of the material of the waveguide and $n_1$ is the refractive index of the adjacent liquid; and (iii) excluding from said measurement substantially all light emerging from said waveguide at an angle that deviates from said optical axis by $|\alpha|$ or more, said method being characterized in that an optical structure comprising a propagating layer of transparent material of refractive index $n_3$ interposed directly between other layers of transparent material of refractive index $n_4$, [the materials of refractive indices $n_3$ and $n_4$ being chosen such that $$n_3^2 - n_4^2 \simeq n_2^2 - n_1^2,$$

and the other layers of material of refractive index $n_4$ being adapted such that the major part of the light passing into them from the propagating layer of refractive index $n_3$ does not pass back into said propagating layer of refractive index $n_3$] is placed close to the edge of said waveguide such that substantially all evanescently coupled light emerging from the edge of said waveguide passes into the said layer of refractive index $n_3$.

In a preferred embodiment of the invention, the external surfaces only of the layers of material of refractive index $n_4$ are coated with a light-absorbing material such that light passing through the layers is significantly attenuated at the interface of the light-absorbing material and the material of refractive index $n_4$. In general, attenuation at the said interface will be such that at least 80% of the light impinging on the interface is absorbed. Other embodiments will be described hereinafter.

It should be understood from the above discussion that the refractive index $n_2$ is greater than $n_1$, and correspondingly $n_3$ is greater than $n_4$.

Although, for reasons of practical convenience, the external surfaces of the layers of material of refractive index $n_4$ of the optical structure are substantially parallel, this is not essential, and the optical structure may take various geometrical forms, e.g. of trapeziform cross-section.

In another aspect, the invention comprises apparatus suitable for carrying out a method of optical analysis as defined above comprising (i) a test object such as a slide or cell located at a test object location, suitable for containing a sample material with fluorescent, phosphorescent or luminescent properties, said test object comprising a transparent solid body, e.g. a sheet or fibre, to act as a waveguide, and to the surface of which the sample material can become bound from a solution or liquid dispersion contacting the solid body; and (ii) an optical structure as defined hereinbefore, which in use can be positioned so that when a test object is at the test object location the optical structure is optically coupled to the transparent solid body of the test object, such that light propagating in the transparent solid body can be received by the optical structure.

In order to minimize degradation of the information contained in the light signal emerging from the transparent solid body as a result of, for example, malformations at the optical edge of said body, it may be desirable for the said body to be optically coupled to the optical structure by means of an index-matching technique.

Thus, in order to reduce scattering of light emerging from an optical edge of an optical waveguide, said optical edge is maintained in intimate contact with an index-matching substance which itself also forms or intimately contacts a further optical component.

By "index-matching substance" is meant a substance having a refractive index similar to that of the material of the waveguide, e.g. having a refractive index differing from that of the waveguide by up to 20%.

Intimate contact between the optical edge and the index-matching substance may be achieved by, for example, selecting an index-matching substance which is a liquid or gel, or by employing precursors for a substantially transparent solid which pliably moulds to the surface of the optical edge before subsequently setting or otherwise solidifying. Examples of suitable index-matching substances include cedar oil, Canada balsam, silicones, ethanol, pentanol, phenylamine, benzene, glycerol, paraffin oil, turpentine, silicone gels, plastics such as silane elastomers, optical cements or adhesives selected from appropriate epoxy and acrylate systems.

The test object may, for example, be a device of the general type described in EP-A-171148.

If desired, the test object (i) and the optical structure (ii) may be coupled together so as to form an integral structure.

The apparatus may further comprise one or more of the following: a photodetector arranged so that, in use, the optical structure is optically coupled to the photodetector, such that light propagating in the optical structure can be received by the photodetector after its emergence;

a light source arranged so that, in use, it can illuminate the test material with light (e.g. at some transverse angle to the principal direction of propagation of the light in the waveguide, for example, at or about 90°), such that light from the test material passes into and through both the transparent solid body of the test object and the optical structure, via total internal reflections to the photodetector; an optical filter (which may be secured in intimate contact with the optical structure) to allow differential transmission through the optical train of the wavelengths of light involved in the method; and a microprocessor or similar processing unit, adapted to analyze in a desired manner the electrical signal emerging from the photodetector.

The invention will be more particularly described hereinafter with reference to fluorescence but it will be understood that analogous considerations apply to phosphorescence or luminescence.

The invention relies on the angular distribution of the light emerging from the waveguide part of the test object, which is dependent on the amounts of fluorophores which are in solution and those which are adsorbed on the surface of said waveguide. Suitable materials for the waveguide are known in the art (see, for example, EP-A-170376 and EP-A-171148) and include, inter alia, glass, silica and plastics materials; in these cases light from material in a liquid adjacent to the waveguide, where said liquid has a refractive index close to that of water, i.e. lower than that of the waveguide, emerges from the waveguide at rather large angles to the axis thereof. Fluorescent, phosphorescent or luminescent molecules bound to the surface of the waveguide can additionally emit light into angles which would be "forbidden" by classical ray optics (i.e. angles greater than the critical angle for the waveguide/sample interface), by the known evanescent wave phenomenon.

In the case of a glass waveguide and an aqueous solution, and fluorescent light of a wavelength of 510 nm, the angle $\alpha$ given by $$\alpha = \arcsin(n_2^2 - n_1^2)^{\frac{1}{2}}$$

is approximately $\pm 47°$. Thus light from an adsorbed layer can be distinguished from that arising from the liquid by the emergence of the former light from the waveguide over a wider range of angles, including angles deviating from the axis of the waveguide by less than about 47°.

The optical structure of the method of the invention leads to enhanced discrimination in use, by guiding substantially all the evanescently coupled light arising from surface-bound fluorophores while causing radiation emerging from the waveguide of the test object at larger angles to be removed. Said optical structure may be placed adjacent to the end of the waveguide of said test object, thereby minimizing loss of fluorescent radiation. The angular discrimination of fluorescence is achieved by use of an optical structure the layers of which are composed of materials of suitably chosen refractive index.

For a better understanding of the present invention, reference is made to the accompanying drawings wherein.

Figure 1:
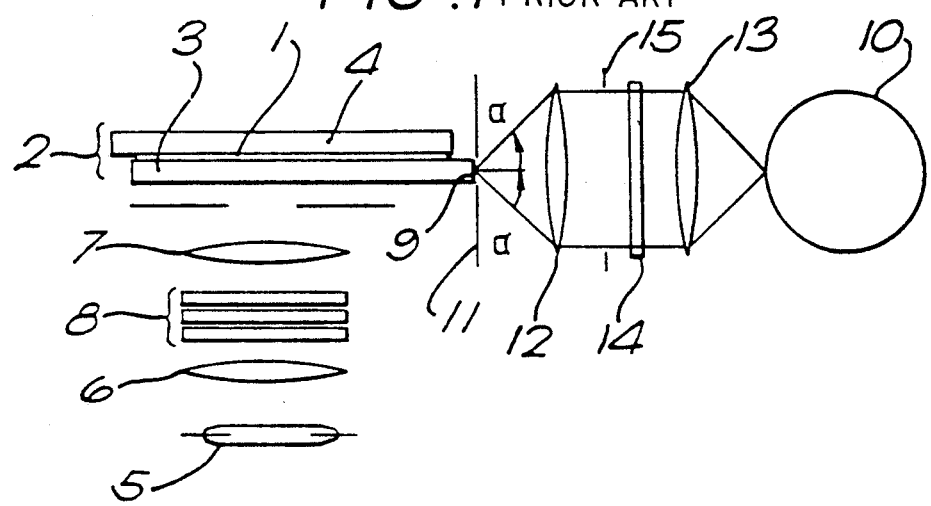
FIG. 1 shows diagrammatically a prior art arrangement for a method of analysis, said arrangement being such as is described in EP-A-170376.

Referring to FIG. 1, the sample liquid 1 is contained within the test object 2, in this case a fluorescence capillary fill device. During the course of the test being carried out, fluorophores within the sample liquid may become bound to a thin layer of material (not shown) at the surface of the waveguide 3 of the test object. The sample liquid 1 is contained in the volume between the layer of material 4 and the waveguide 3. In the embodiment shown in FIG. 1, illumination is provided by a light source 5, whose output may be focused using lenses 6, 7 and filtered by means of a filter stack 8 to provide light of suitable excitation wavelength. The waveguide 3 has an edge 9 which is substantially both smooth and perpendicular to the long dimensions. Light from the liquid 1 and from the surface layer may propagate through the waveguide with multiple internal reflections, emerging from the edge 9. Light emerging directly out of the device arising from the liquid sample is removed by means of a mask 11 with an aperture. A photodetector 10 is disposed so that it receives light emerging from the edge 9 which diverges from the long axis of the waveguide by an angle whose magnitude is not greater than $\alpha$ as defined hereinbefore. This is achieved by screening by, for example, an apertured screen 15, with which may be associated one or more convex lenses 12, 13 to collect the light exiting over the desired angular range on to the photodetector. Light emerging from the edge 9 may be filtered by means of a filter 14 so that light of excitation wavelength may be excluded from reaching the detector 10.

It should be emphasized that FIG. 1 shows the arrangement of apparatus diagrammatically. As a practical matter, it would in this prior art arrangement be preferable for efficient detection to have a 45° prism (not shown) in contact with the edge 9 as the first element in the optical detection train.

Figure 2A:
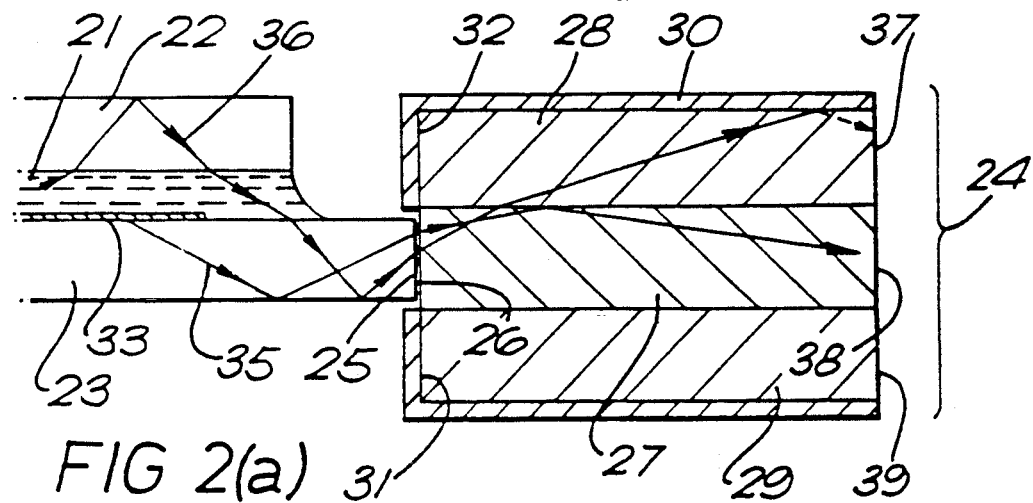
FIG. 2(a) shows by means of a diagrammatic section how, in use, optical coupling between the test object as hereinbefore described and one embodiment of an optical structure as hereinbefore described leads to angular discrimination of fluorescence.

FIG. 2 shows how the present invention may lead to enhanced discrimination between light arising from surface-bound fluorophores and light arising from fluorophores in the sample liquid, whilst greatly simplifying the optical train. As in FIG. 1, the sample liquid 21 of refractive index $n_1$ is contained within the layer 23 of solid transparent material of refractive index $n_2$ and the layer 22, layer 23 being suitable to act as a waveguide. An optical structure 24 is positioned close to the edge 25 of the waveguide such that substantially all the light impinging on the edge 25 of the waveguide passes into the propagating layer 27 of solid material of refractive index $n_3$ contained within the optical structure, via the end aperture 26. In general, the thickness of layer 27 should be greater than or equal to the thickness of layer 23 for optimum optical coupling.

Under certain circumstances it may be desirable to extend the opaque coating 30 over the ends 31 and 32 of the optical structure 24 to define the aperture to be of the same dimensions as, or smaller than, the optical edge 25.

The material of the propagating layer 27 will in general have a refractive index $n_3$ which is greater than $n_2$, but this is not essential. Suitable materials for the layer 27 include, for example, optical glass, silica, phosphate glasses and polymeric materials such as crystal styrene. In some embodiments it may be desirable that layer 27 be a liquid, confined within the optical structure 24 by suitable means (e.g. thin layers of strong transparent material at the ends). Disposed on either side of propagating layer 27 are other layers 28 and 29 of transparent solid material, both layers usually having refractive index $n_4$, whose external surfaces are in this embodiment coated with a light-absorbing coating 30. Alternatively, layers 28 and/or 29 may be a liquid confined within the optical structure 24 by suitable means, provided always that no total internal reflection occurs at the interface between the liquid and its confining means.

Figure 2B:
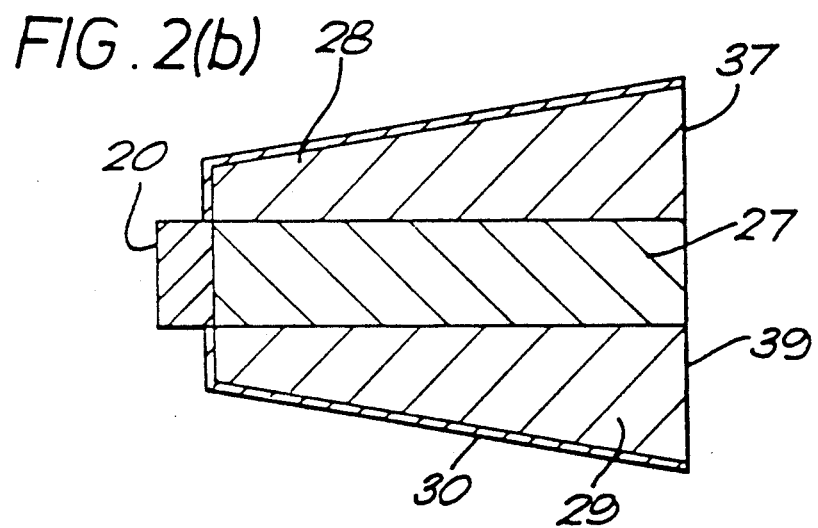
FIG. 2(b) shows an alternative embodiment of the optical structure.

In the embodiment shown, it is essential that the external surfaces of the optical structure which are substantially parallel to the long axis of said structure should be substantially totally coated with the coating 30, for reasons to be discussed hereinbelow. It is also desirable, but not essential, that the coating 30 extends to cover the ends 31 and 32 of the layers 28 and 29. As an alternative, a physical aperture could be used, to cover ends 31 and 32 of the optical structure when in use. It is by no means essential that the external surfaces of the optical structure are parallel to the long axis thereof. Thus, by way of example, as shown in FIG. 2(b), an optical structure may be produced which has a cross-section the shape of a trapezium.

It is also desirable, but not essential, that the coating 30 extends to cover the ends 37 and 39 of the layers 28 and 29. As an alternative, a physical aperture could be used, to cover ends 37 and 39 of the optical structure when in use.

Suitable materials for layers 28 and 29 include silica, magnesium fluoride, lithium fluoride, optical glasses (e.g. BK7 or crown glass), phosphate glasses, polymeric materials (e.g. acrylic or silicones) and liquids. For suitable materials (e.g. phosphate glasses), the layers 28 and 29 may, if desired, be applied by spin-coating. The thickness of the layers 28 and 29 should be greater than 2 microns.

The choice of materials for the layers 27, 28 and 29 is important to the success of the method of the invention. In use, the angular discrimination of light 35 arising from fluorophores bound to the surface 33 from light 36 arising from the sample liquid 21 is achieved by careful choice of refractive indices $n_3$ and $n_4$. In general, these will be such that $$n_3^2 - n_4^2 \approx n_2^2 - n_1^2.$$

In some circumstances, however, it may be desirable that the quantity ($n_3^2 - n_4^2$) is rather less than suggested by the above equation; this will have the effect of causing less of the light emerging from end 25 to be collected by the photodetector from the optical structure 24, particularly at angles close to $\alpha$ as defined hereinbefore.

Suitable materials for the light-absorbing coating 30 include black paint, optionally curable by heat or infrared radiation, silicone paint, dyes, etc., which may be applied by conventional methods such as screen printing or, if appropriate, by spin-coating or spraying. Such materials should attenuate or absorb light at least at the wavelengths involved in the assay. The minimum thickness of the coating 30 will typically be 3 microns. The optical structure 24 performs the same role as the components 11-15 of FIG. 1 but is much more convenient to use. Furthermore, in contrast to the prior art situation in which a prism was placed in contact with the optical edge of the waveguide, there is in the present invention no necessity for the optical structure as herein defined to be in contact with the said edge: an intervening gap of several millimetres (when using the apparatus described in Example 1 hereinafter) may be present without serious loss of sensitivity.

In a further embodiment, the external surfaces of the layers 28 and 29 of the optical structure 24 may be roughened, so that light refracted into layers 28 and 29 is scattered out of the optical structure 24. In such an embodiment, it is preferred that the external surfaces of layers 28 and 29 be roughened such that substantially all of the light refracted into layers 28 and 29 is scattered out of the optical structure 24. In such circumstances it may be desirable, but not essential, to apply a coating 30 to the optical structure 24 as already described. In an alternative embodiment, light refracted into layers 28 and 29 may be scattered out of the optical structure 24 by providing that the external surfaces of the layers take the form of suitable diffraction gratings.

In a still further embodiment, the thicknesses of the layers 28 and 29 may be sufficiently great that substantially no light propagating in layers 28 and 29 can re-enter layer 27. In such an embodiment it is preferred that layers 28 and 29 be sufficiently thick that substantially no light propagating therein re-enters layer 27. In such a case the thickness h of layer 28 and/or 29 is given by $$h > \tfrac{1}{2}d(n_4^2 - 1)^{\tfrac{1}{2}}$$

where d is the length of the optical structure and $n_4$ is defined as hereinbefore. In such circumstances it may still be desirable, but not essential, to apply a coating 30 to the optical structure 24 as already described.

An optical filter (e.g. of colloidal glass) may optionally be incorporated either into or onto the optical structure 24 at the end 26. If the optical filter is incorporated into the optical structure 24 (as in the particular embodiment illustrated in FIG. 4) then it should preferably be made of material having the same, or higher, refractive index as layer 27. When a filter glass of appropriate refractive index cannot be found, the filter 20 may be bound onto the end 26 of layer 27, as is shown in the embodiment of FIG. 2(b). As a result of the optics of the method of the present invention, any secondary fluorescence arising in this filter and transmitted to the photodetector is minimized. Alternatively, the optical filter can be incorporated either into or onto the optical structure at the end 38.

If the presence of interference filters were desirable in the detection optics, for example to reduce spurious fluorescence and/or phosphorescence arising within the device, suitable multilayer filters could be deposited onto the face 26 and/or the face 38 of the optical structure 24, for example by means of vacuum deposition techniques known per se. Alternatively a pre-formed interference filter may be optically coupled onto the face 26 and/or the face 38 of the optical structure.

Figure 3A:
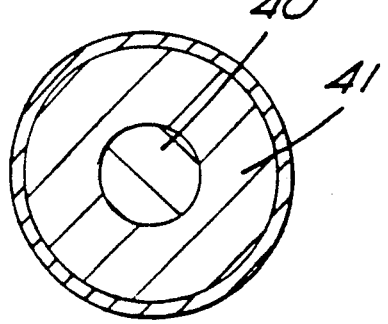
FIG. 3 shows (a) a transverse cross-section and 3(b) a longitudinal cross-section through an alternative optical structure which may be employed in accordance with the invention.

FIG. 3(a) shows a transverse cross-section through a cylindrical variant of the optical structure to be used in accordance with the invention. A cylindrical propagating layer 40 of material of refractive index $n_3$ is surrounded by a coaxial other layer 41 of material of refractive index $n_4$. As previously described, the external surfaces of the layer 41 are coated with a suitable opaque material.

Figure 3B:
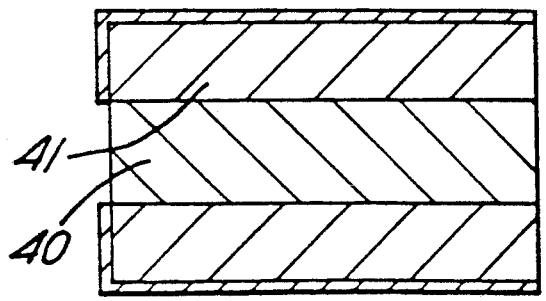

FIG. 3(b) shows a longitudinal cross-section through this variant, which accords with the structure shown in FIG. 2.

Cylindrical structures such as shown in FIG. 3(a) and 3(b) can advantageously be used in conjunction with cylindrical biosensors such as described, for example, in U.S. Pat. No. 4,447,546.

In use, the photodetector as hereinbefore described, e.g. a photomultiplier tube, could be placed close to the end of the optical structure from which the fluorescent light emerges, so as to detect directly the light emerging from said optical structure without necessity for additional lenses. Such an arrangement would minimize loss of signal due to reflection. However, if desired, additional lenses may be used as in conventional methods.

An alternative arrangement may be to optically couple a suitable photodetector (e.g. a silicon photodetector) to the end face 38 of the optical structure 24.

The discussion above is made with particular reference to immunoassays involving fluorescence capillary fill devices (FCFD's), but it is to be understood that the invention applies also to other methods and devices which involve angular discrimination of optical signals emerging from waveguides, particularly those involving evanescent signals.

The method of the invention is particularly applicable to assays e.g. of antigens or antibodies, i.e. to immunoassays. However, the invention is not to be taken as limited to assays of antibodies or antigens. Examples of ligands which may be assayed in conjunction with the method of the invention are given in Table 1 below, together with an indication of a suitable specific binding partner in each instance.

TABLE 1

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used in conjunction with assays of: hormones, including peptide hormones (e.g. thyroid stimulating hormone (TSH), luteinising hormone (LH), human chorionic gonadotrophin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxins, vitamins, proteins, viruses such as influenza, para-influenza, adeno-, hepatitis, respiratory and AIDS viruses, or microorganisms.

The following non-limiting Example is intended to illustrate the invention.

EXAMPLE 1

An Optical Immunoassay for Human Chorionic Gonadotrophin

Preparation of Starting Materials (i) Fabrication of an optical structure

Figure 4:
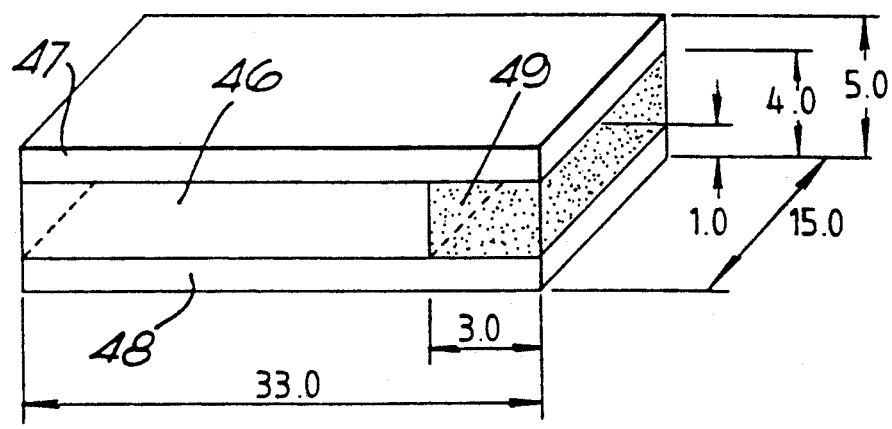
FIG. 4 shows in detail an optical structure fabricated for use in accordance with the present invention.

FIG. 4 shows in more detail an optical structure of the type shown in FIGS. 2 and 3, fabricated for use in accordance with the invention as follows:

From a plate of Souriel B89/61 optical glass, a piece 46 of dimensions 30.0 mm × 15.0 mm × 3.0 mm was cut using conventional techniques. After polishing all the surfaces of the glass, again using conventional techniques, the glass was glued to two pieces 47,48 of silica (33.0 mm × 15.0 mm × 1.0 mm) which had been cut and polished using standard methods. The adhesive used to bond the layers was Lensbond optical cement (refractive index 1.55). A piece 49 of filter glass (OG 515 colloidal glass), having been cut to the correct dimensions (15.0 mm × 3.0 mm × 3.0 mm) and polished in the normal manner, was glued into the optical structure, using the same adhesive as before. Finally, all the exposed silica surfaces (but not those of either the optical glass or the filter glass) of the optical structure were spray-painted with a black opaque coating (not shown).

(ii) Preparation of anti-hCG antibody conjugated to fluorescein isothiocyanate (FITC)

200 mg of FITC (Sigma Chemical Company Ltd., UK) and 5 mg of a second monoclonal antibody to hCG specific for a different antigenic determinant were mixed together in 1.4 ml of 0.2 M sodium bicarbonate buffer solution (pH 9.0). The mixture was left for 18 hours at room temperature, during which conjugation of FITC to the monoclonal antibody occurred. The mixture was then purified by gel filtration on Sephadex G-50 superfine.

(iii) Preparation of hCG standard solutions

A freeze-dried preparation of hCG calibrated against the first international reference preparation (75/537) was obtained from Biodata SpA, Milan, Italy. This sample was diluted in horse serum (Serono Diagnostics Ltd., Woking UK) to give the range of hCG standards required.

(iv) Apparatus used in the measurement of the hcg assay

For the assay according to the present invention, components corresponding to labels 1–10 of FIG. 1 were used. The test object 2 was a fluorescence capillary fill device of a type disclosed in EP-A-171148, on the internal surface of the waveguide part 3 of which was immobilized by conventional methods a monoclonal antibody against hCG. The light source 5 was a Heinmann Xenon flash lamp. The filter stack 8 comprised three filters: a BG7 Schott glass filter (Ealing Electro Optics UK Ltd., Watford UK), a 450–480 nm FITC bandpass interference filter (Optometrics Ltd., UK) and a 475 nm shortpass interference filter (Comar Instruments Ltd., Cambridge UK).

The optical structure fabricated as in paragraph (i) above was placed adjacent to the edge 9 of the waveguide (see also FIG. 2). The photodetector 10 was a Hamamatsu R931A photomultiplier tube (Hakuto UK Ltd).

For comparison, a conventional assay using components labelled 11–15 in FIG. 1 was also carried out. In this latter case, the filter 14 used was a Schott OG515 515 nm colloidal glass filter.

Assay Methodology

The αhCG-FITC conjugate was added to each of the hCG standards to give about 0.5 ml of test solution. The conjugate concentration was 1 μg/ml. Test cells were chosen and each was filled with a different test solution. The signal from the photodetector was recorded after a 20-minute incubation period in a humid environment at 20° C.

Figure 5:
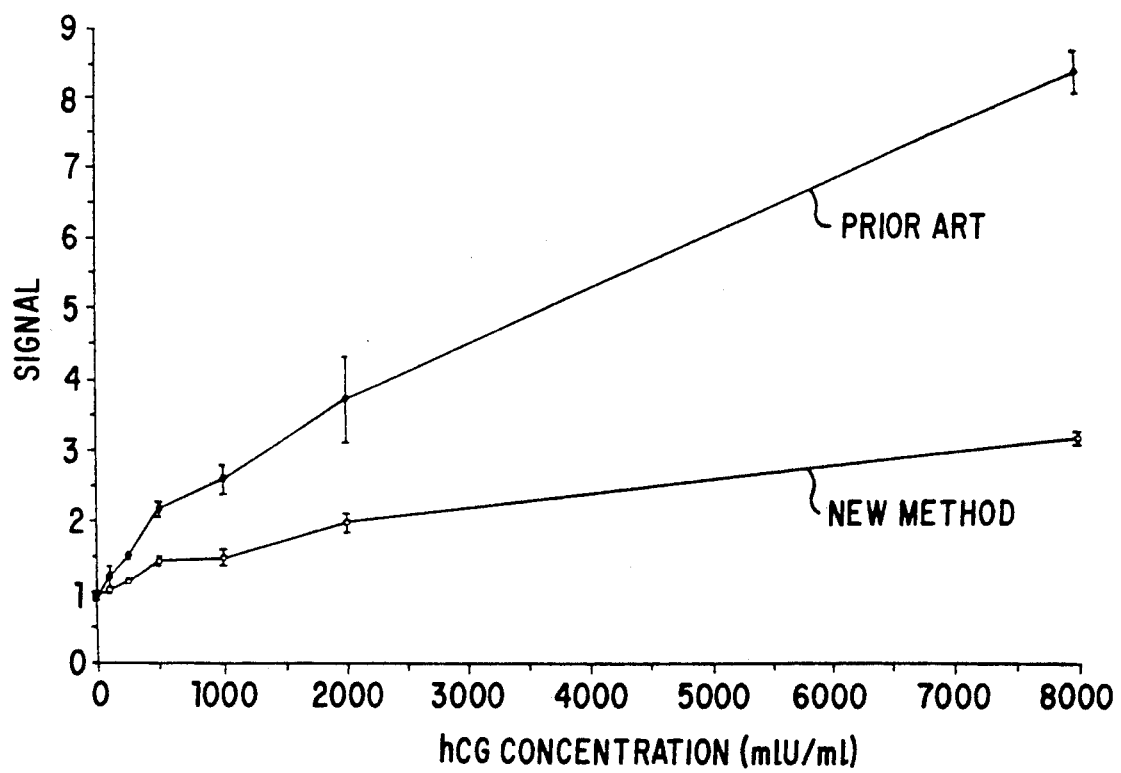
FIG. 5 shows graphically the results of an assay carried out in accordance with the invention.

FIG. 5 shows graphically the results of an assay carried out using apparatus including an optical structure as described hereinbefore, in comparison with results from a conventional assay using apparatus shown schematically in FIG. 1. The assay carried out in accordance with the present invention exhibits significantly better precision than the prior art (5.1% compared with 9.0%).

I claim:

1. In a method of optical analysis of a test sample labelled with a light emitting fluorescent, phosphorescent or luminescent material, a part of said test sample being bound, directly or indirectly, to the surface of an optical waveguide in contact with sample liquid, said method comprising measuring light emitted from the bound test sample which has entered and propagated through said waveguide and emerged from an edge thereof at an angle less than $\alpha$ relative to the optical axis of said waveguide, wherein $$\alpha \approx \arcsin(n_2^2 - n_1^2)^{\frac{1}{2}},$$

$n_2$ is the refractive index of the waveguide and $n_1$ is the refractive index of the sample liquid, the improvement comprising placing an optical structure close to the edge of said waveguide so as to collect light emerging therefrom prior to said measuring, said optical structure comprising a propagating layer of transparent material of refractive index $n_3$ interposed between other layers of transparent material of refractive index $n_4$, $n_3$ and $n_4$ being such that $$n_3{}^2 - n_4{}^2 \approx n_2{}^2 - n_1{}^2,$$

the propagating layer being constructed so as to collect light emerging from aid waveguide and propagate that portion of light emerging from said waveguide at an angle less than $\alpha$, and the other layers being constructed so that the major part of the light passing into them from the propagating layer, which light is desired to be excluded from said measuring, does not pass back into the propagating layer, and measuring the light propagated through the propagating layer.

2. A method according to claim 1 wherein at least one surface of the other layers of refractive index $n_4$ not in contract with the propagating layer of refractive index $n_3$ is coated with a light-absorbing material.

3. A method according to claim 2 wherein at least 80 percent of the light impinging on the light-absorbing material is absorbed.

4. A method according to claim 1 wherein at least one surface of the other layers of refractive index $n_4$ not in contact with the propagating layer of refractive index $n_3$ is roughened such that light impinging on said surface is scattered out of the optical structure.

5. A method according to claim 4 wherein said surface is coated with a light-absorbing material.

6. A method according to claim 1 wherein the propagating layer of refractive index $n_3$ is cylindrical and the other layer of refractive index $n_4$ is a surrounding coaxial cylinder.

7. A method according to claim 1 wherein the thickness h of the other layers of refractive index $n_4$ is given by $$h > \tfrac{1}{2}d(n_4{}^2 - 1)^{\tfrac{1}{2}}$$

where d is the length of the optical structure.

8. A method according to claim 1 wherein said waveguide is optically coupled to said optical structure via an index-matching substance in intimate contact with said waveguide and said optical structure.

9. Apparatus for use in a method of optical analysis of a test sample labelled with a fluorescent, phosphorescent or luminescent material comprising:

a test object comprising an optical waveguide constructed so as to bind said test sample directly or indirectly to the surface thereof from a sample liquid in contact therewith; and an optical structure which in use is positioned close to the edge of said waveguide so as to collect light emerging therefrom, said optical structure comprising a propagating layer of transparent material of refractive index $n_3$ interposed between other layers of transparent material of refractive index $n_4$, $n_3$ and $n_4$ being such that $$n_3{}^2 - n_4{}^2 \approx n_2{}^2 - n_1{}^2,$$

wherein $n_2$ is the refractive index of the waveguide and $n_1$ is the refractive index of the sample liquid, the propagating layer being constructed so as to collect light emerging from said waveguide and propagate that portion of light emerging from said waveguide at an angle less than $\alpha$ relative to the optical axis of said waveguide, wherein $$\alpha \approx \arcsin(n_2{}^2 - n_1{}^2)^{\tfrac{1}{2}},$$

and the other layers being constructed so that the major part of the light passing into them from the propagating layer does not pass back into said propagating layer.

10. Apparatus according to claim 9 wherein the test object comprises a cavity having a dimension small enough to enable sample liquid to be drawn into the cavity by capillary action, one surface of the cavity being the surface of said optical waveguide, said surface carrying an immobilized reagent which directly or indirectly binds said test sample.

11. Apparatus according to claim 10 wherein said optical waveguide is a transparent solid plate having an edge which is substantially optically smooth and transverse to the plane of the plate.

12. Apparatus according to claim 10 wherein the test object and the optical structure are coupled together so as to form an integral unit.

13. Apparatus according to claim 10 wherein said optical structure is optically coupled to said waveguide via an index-matching substance in intimate contact with said optical structure and said waveguide.

14. Apparatus according to claim 9 wherein at least one surface of the other layers of refractive index $n_4$ not in contact with the propagating layer of refractive index $n_3$ is coated with a light-absorbing material.

15. Apparatus according to claim 9 wherein at least one surface of the other layers of refractive index $n_4$ not in contact with the propagating layer of refractive index $n_3$ is roughened such that light impinging on said surface is scattered out of the optical structure.

16. Apparatus according to claim 15 wherein said surface is coated with a light-absorbing material.

17. Apparatus according to claim 9 wherein the propagating layer of refractive index $n_3$ is cylindrical and the other layer of refractive index $n_4$ is a surrounding coaxial cylinder.

18. Apparatus according to claim 9 wherein the thickness h of the other layers of refractive index $n_4$ is given by $$h > \tfrac{1}{2}d(n_4{}^2 - 1)^{\tfrac{1}{2}}$$

where d is the length of the optical structure.

* * * * *